US012054892B2

(12) United States Patent
Wuori

(10) Patent No.: US 12,054,892 B2
(45) Date of Patent: Aug. 6, 2024

(54) DIELECTRIC PROFILE EXHAUST DRYING SYSTEM

(71) Applicant: Bryce Wuori, Bismarck, ND (US)

(72) Inventor: Bryce Wuori, Bismarck, ND (US)

( * ) Notice: Subject to any disclaimer, the term of this patent is extended or adjusted under 35 U.S.C. 154(b) by 536 days.

(21) Appl. No.: 17/409,961

(22) Filed: Aug. 24, 2021

(65) Prior Publication Data

US 2023/0060768 A1 Mar. 2, 2023

(51) Int. Cl.
*E01C 19/28* (2006.01)
*E01C 23/01* (2006.01)
*E01C 23/14* (2006.01)
*G01N 9/36* (2006.01)
*E01C 19/26* (2006.01)

(52) U.S. Cl.
CPC ............. *E01C 23/01* (2013.01); *E01C 23/14* (2013.01); *G01N 9/36* (2013.01); *E01C 19/26* (2013.01)

(58) Field of Classification Search
CPC .......... E01C 19/26; E01C 19/28; E01C 23/01; E01C 23/14; G01N 9/36
USPC ....................................... 404/75, 77, 95, 119
See application file for complete search history.

(56) References Cited

U.S. PATENT DOCUMENTS

| | | | | |
|---|---|---|---|---|
| 3,874,366 A * | 4/1975 | Cutler | ...................... | E01C 23/14 126/271.2 A |
| 4,793,730 A * | 12/1988 | Butch | ................... | E01C 23/065 404/91 |
| 7,226,239 B2 * | 6/2007 | Stridiron | ............... | E01C 19/288 404/84.1 |
| 7,731,450 B2 * | 6/2010 | Congdon | .............. | E01C 19/288 701/50 |
| 8,418,448 B2 | 4/2013 | Kamata | | |
| 2005/0183512 A1 * | 8/2005 | Corcoran | ................ | E02D 3/026 73/818 |
| 2012/0111003 A1 | 5/2012 | Kasuya | | |
| 2016/0103051 A1 * | 4/2016 | Corcoran | .................. | E01C 3/04 73/32 R |
| 2019/0094202 A1 | 3/2019 | Troxler | | |
| 2023/0175211 A1 * | 6/2023 | Saarenketo | .......... | G01N 33/246 404/75 |

FOREIGN PATENT DOCUMENTS

| | | |
|---|---|---|
| DE | 102011114709 A1 | 4/2013 |
| FR | 2868809 A1 | 10/2005 |
| WO | 2009080154 A2 | 7/2009 |

OTHER PUBLICATIONS https://ict.illinois.edu/news/newsletters/more-newsletters/august-2021/al-qadi-to-lead-FHWA-project-on-ground-penetrating-radar; Illinois Center for Transportation Al-Qadi to lead FHWA project on ground-penetrating radar Webpage; Received Aug. 3, 2021.

* cited by examiner

*Primary Examiner* — Raymond W Addie
(74) *Attorney, Agent, or Firm* — Fargo Patent & Business Law; Thomas Kading

(57) ABSTRACT

A profiling mount device for redirecting the exhaust energy of a compactor onto an asphalt surface and a method to use it. The profiling mount device to cause surface moisture located on the asphalt surface to be dried. A dielectric sensor is attached to the profiling mount device such that it can take a dielectric constant reading at the desired location where the exhaust energy dries the asphalt surface. The dielectric constant reading is taken by a dielectric profiling system (DPS). The dielectric profiling system cannot accurately read the dielectric constant of an asphalt section when surface moisture is present.

11 Claims, 5 Drawing Sheets

DIELECTRIC PROFILE EXHAUST DRYING SYSTEM

FIELD OF TECHNOLOGY

This disclosure relates generally to technology for asphalt paving operations and more particularly to using an asphalt roller and sensors to test asphalt.

BACKGROUND

Compaction equipment is used to compress new asphalt pavement which is laid. Asphalt is compacted to certain specifications based on engineering and design requirements. Specifications often call for compaction such that a required density is achieved. Asphalt density is a measurement taken to derive the percentage air voids in asphalt to determine the structural integrity of the section compacted. A commonly desired density range is between 92-96%. In the event the density is too low, the asphalt may need to be removed and replaced or contractor can take large deductions in payment. Both options are costly for the contractor or owner of the project. Alternatively, if the density is too high, the asphalt may be weakened and may be of less value to the contractor or owner of the project. Structurally, it is thought that the asphalt is weakened from lack of air voids that allow the asphalt to be flexible during seasonal freeze-thaw cycles when the density is too high.

In a roadway application, asphalt is commonly laid by a mechanical paver after which compaction is performed by one or more compactors. Compaction is often performed in a compaction train or by three separate compaction rollers. Each of these compactors have a separate role in the overall compaction process. The first stage is the knockdown roller, the second is the intermediate roller, and the third is the final or correction roller. The dielectric constant is measured after the final roller or on the correction roller. Before taking a dielectric constant reading, the asphalt surface must be dried of surface moisture. Traditionally, the asphalt is let to cool to a temperature of about 48.8 degrees Celsius (120 degrees Fahrenheit) or less prior to taking a dielectric constant reading. By allowing the asphalt to cool, the asphalt is given time to dry. Asphalt cures at a temperature of 60 degrees Celsius (140 degrees Fahrenheit) to 65.5 degrees Celsius (150 degrees Fahrenheit). By allowing the asphalt to cool to 48.8 degrees Celsius, the asphalt is cured and cannot be further compacted. Further, delaying the dielectric constant reading until the asphalt is cooled, results in the paver laying asphalt at a significant distance ahead of where the reading is being taken. This means that any adjustment to be made with the asphalt installation process is not applied over the asphalt installed between the place where the reading is taken and where the paver is located.

A dielectric constant reading is commonly taken by a dielectric profiling system (DPS). DPS technology is commonly appreciated by persons of ordinary skill in the art for testing asphalt. DPS technology is inaccurate when surface moisture is present on the asphalt surface. It has been long desired to establish technology which can adequately dry the asphalt surface such that a dielectric constant reading can be taken shortly after or contemporaneously with a compactor completing compaction. Many attempts have been made to accomplish the desired technology, but none have succeeded.

SUMMARY

This disclosure is directed toward an asphalt drying device mounted on a compactor to prepare an asphalt surface for testing using a dielectric profiling system, and a method to use. The device in this application is referred to as a profiling mount device. The profiling mount device uses exhaust energy from the asphalt roller which is redirected at the asphalt surface which is to be tested using a dielectric profiling system. The exhaust energy which is redirected on the asphalt surface dries surface moisture from the asphalt surface. Moisture on the surface needs to be removed prior to testing using a dielectric profiling system.

A dielectric profiling system is used for assessing asphalt compaction quality without using destructive coring techniques. Coring techniques are further not reflective of an entire installation of an asphalt section. The dielectric profiling system has a dielectric sensor which takes a reading of the dielectric constant at a desired location on the asphalt surface. The dielectric sensor is attached to the profiling mount device.

The profiling mount device comprises a connection point, an angled pipe, a tip, and a dielectric mount. The connection point attaches to the exhaust port of a compactor. Typically, the compactor upon which the profiling mount device attaches will be a finish or correction roller. Exhaust energy flows out the compactor's exhaust port, through the connection point, through the angled pipe, and subsequently out the tip. The angled pipe is shaped such that the exhaust energy which flows through, is redirected towards the asphalt surface through the tip. The tip is shaped such to allow the exhaust energy to be emitted upon the desired location on the asphalt surface at which the dielectric sensor will take a reading of a dielectric constant. The dielectric mount is configured such to allow a dielectric sensor to be attached in a manner which allows the dielectric sensor to take readings at a desired location on the asphalt surface.

The exhaust energy which is emitted through the profiling mount device is often diesel exhaust which is expressed from a diesel engine. Diesel exhaust emitted from the tip is flowing at a rate that assists in blowing surface moisture off the asphalt surface, and further is emitted at a temperature that causes surface moisture to dry.

The profiling mount device allows a dielectric constant to be measured contemporaneously with a compactor traveling over an asphalt surface. This allows for dielectric sensor readings to be taken much sooner after a paver lays asphalt than traditional dielectric constant reading methods. Traditionally, dielectric constant reading methods which wait for the asphalt to cool to a temperature of about 48.8 degrees Celsius (120 degrees Fahrenheit) often cause the dielectric constant readings to be taken at a distance of over 1,000 meters (3,280 feet) from the paving train. The profiling mount device allows for dielectric readings to be taken at a smaller distance from the paving train. For example, the profiling mount device can result in a dielectric constant reading being taken at a distance of 152 meters (500 feet) from the paving train.

BRIEF DESCRIPTION OF THE DRAWINGS

These and other features and advantages of the present invention will become more readily appreciated as the same becomes better understood by reference to the following detailed description when considered in connection with accompanying drawings, wherein.

DETAILED DESCRIPTION OF THE ILLUSTRATED EMBODIMENTS

General

The present invention will now be described with occasional reference to the specific embodiments of the invention. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. The terminology used in the description of the invention herein is for describing particular embodiments only and is not intended to be limiting of the invention. As used in the description of the invention and the appended claims, the singular forms "a," "an," and "the" are intended to include the plural forms as well, unless the context clearly indicates otherwise.

Unless otherwise indicated, all numbers expressing quantities of dimensions such as length, width, height, and so forth as used in the specification and claims are to be understood as being modified in all instances by the term "about." Accordingly, unless otherwise indicated, the numerical properties set forth in the specification and claims are approximations that may vary depending on the desired properties sought to be obtained in embodiments of the present invention. Notwithstanding that the numerical ranges and parameters setting forth the broad scope of the invention are approximations, the numerical values set forth in the specific examples are reported as precisely as possible. Any numerical values, however, inherently contain certain errors necessarily resulting from error found in their respective measurements.

Figures Detail

Figure 1:
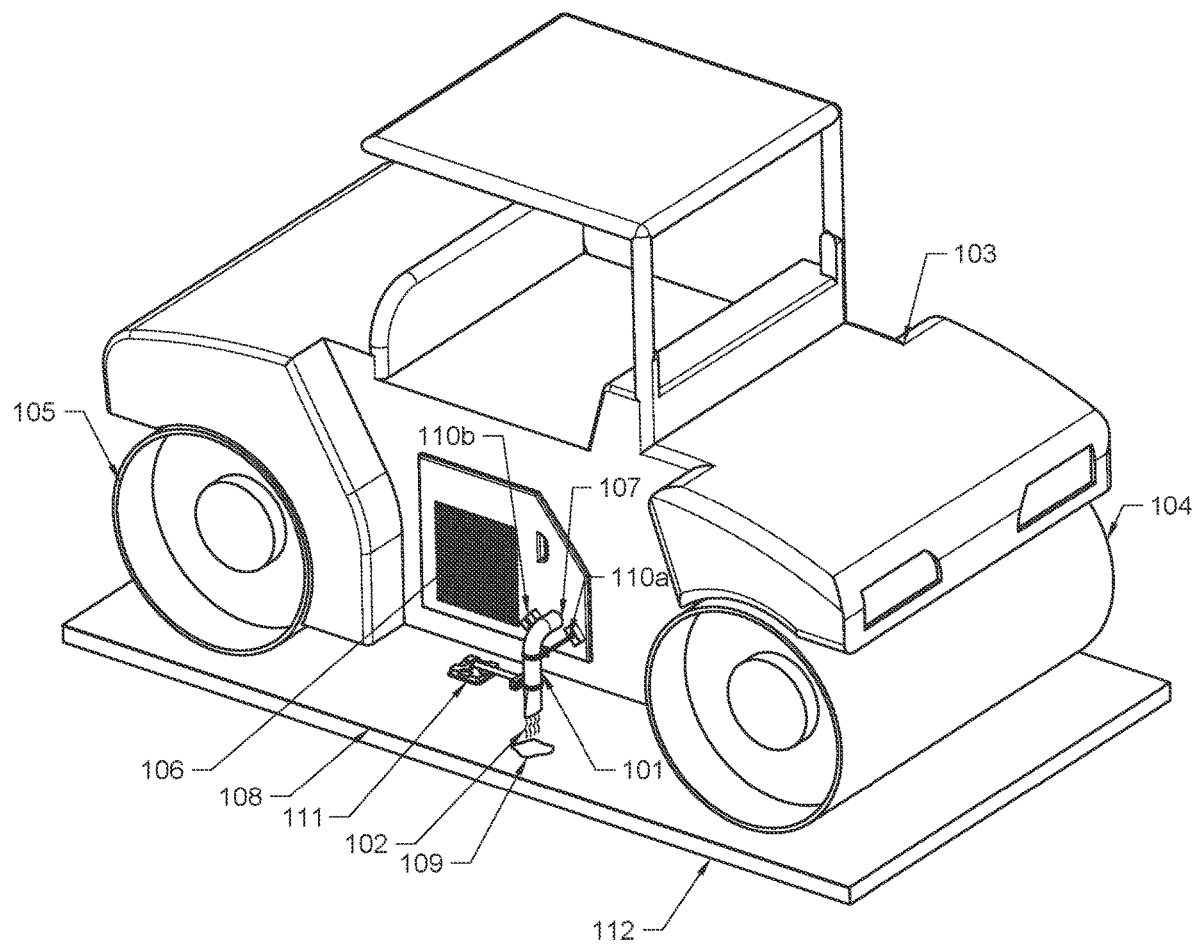
FIG. 1 is a 3D perspective of a compactor with a profiling mount device attached.

FIG. 1 is a 3D perspective of a compactor 103 with a profiling mount device 101 attached. The compactor 103 in this exemplary embodiment comprises a front roller 104, a rear roller 105, a power unit 106, and an exhaust port 107. The front roller 104 and rear roller 105 may be configured in alternative embodiments as appreciated by one of ordinary skill in the art. For example, a compactor may be configured with a single roller, a static roller, a vibratory roller, a smooth roller, a pneumatic roller, or other similar devices. Further, the compactor may be of any size used for asphalt compression. Alternatively, the profiling mount device 101 may be mounted on a piece of equipment other than a compactor. For example, the profiling mount device 101 could be attached to a skid steer or road grader.

The front roller 104 as shown in FIG. 1 is a smooth roller used for compressing recently installed asphalt. The rear roller 105 in the exemplary embodiment is also a smooth roller. The power unit 106 is attached to the compactor 103 and is used by the compactor 103 to drive the compactor 103 and provide power to the compactor's functions. The power unit 106 as used in an exemplary compactor 103 is a diesel engine that expresses diesel exhaust as its exhaust energy. The power unit 106 may also be configured as a gasoline engine, an electric motor, or any other device capable of powering the compactor 103 and expressing exhaust energy. The exhaust energy is expressed from the power unit 106 in the form of exhaust 102. When the power unit 106 is a diesel engine embodiment, the exhaust energy is in the form of exhaust 102 from the combustion of the diesel fuel. The exhaust 102 is expressed from the diesel engine through an exhaust manifold and away from the compactor 103 through an exhaust port 107.

The profiling mount device 101 is attached to the exhaust port 107 through which exhaust 102 is emitted. The profiling mount device 101 is attached in a way that it is sealed to the exhaust port 107 such that exhaust 102 is redirected by the profiling mount device 101. In the FIG. 1 exemplary embodiment the exhaust 102 is redirected from the exhaust port 107 downward to the asphalt surface 108. The asphalt surface 108 is considered to be the topmost surface of an asphalt section 112. Exemplary surface moisture 109 is shown on the asphalt surface 108 at the location where the profiling mount device 101 redirects the exhaust 102.

In the FIG. 1 exemplary embodiment the profiling mount device 101 is secured to the exhaust port 107 and the compactor 103 using two different manners. The two manners shown and described herein are not the exclusive manner in which the profiling mount device 101 may be attached. Any manner appreciated by a person with ordinary skill in the art may be used. In the exemplary embodiment, a front mounting bracket 110a and a rear mounting bracket 110b mechanically attach the profiling mount device 101 to the compactor 103. The front mounting bracket 110a and the rear mounting bracket 110b are referred to as the mounting brackets 110. The profiling mount device 101 can be sealed to the exhaust port 107 using welding methods, clamps, or other appreciated methods.

In FIG. 1 the mounting brackets 110 are attached to the compactor 103 on one respective end, and attached to the profiling mount device 101 on the other respective end. In the exemplary embodiment two mounting brackets 110 are used. The mounting brackets 110 can help stabilize the profiling mount device 101 from vibration caused by the compactor 103.

Exhaust 102 redirected by the profiling mount device 101 which is directed upon surface moisture 109 causes the surface moisture 109 to be dried from the asphalt surface 108. The drying occurs from the exhaust which the power unit 106 is expressing and the profiling mount device 101 is emitting through the tip 202. A dielectric sensor 111 is attached to the profiling mount device 101 in such a way that the dielectric sensor 111 can take a reading measurement at the location on the asphalt surface 108 which has been dried of surface moisture 109 by exhaust 102 directed by the profiling mount device 101.

A dielectric sensor 111 is a component of a dielectric profiling system that measures the dielectric constant at a location on the asphalt section 112. The measurement of the dielectric constant may be done using any method understood by a person of ordinary skill in the art. The measurement of the dielectric constant in an asphalt section is a commonly understood technique. When an asphalt section is installed and subsequently compressed, the process results in moisture being on the asphalt surface. Measuring the dielectric constant in an asphalt section has not been possible until surface moisture on the asphalt surface has dried. Given this constraint, it has not been possible to measure the dielectric constant in an asphalt section contemporaneously as the asphalt is being compressed by a compactor 103.

A dielectric constant reading is used to determine the density of an asphalt section. The dielectric constant does not directly equate to a specific density until a calibration is performed. Once calibrated, the dielectric constant can be used to indicate the density.

A dielectric sensor 111 is commonly calibrated one or more times per day. As conditions change throughout a day, the dielectric sensor 111 is calibrated. Calibration takes into account elevation, air pressure, density, temperature, and other such factors. A common method to perform calibration includes the use of a steel plate or HDPE puck.

Figure 2:
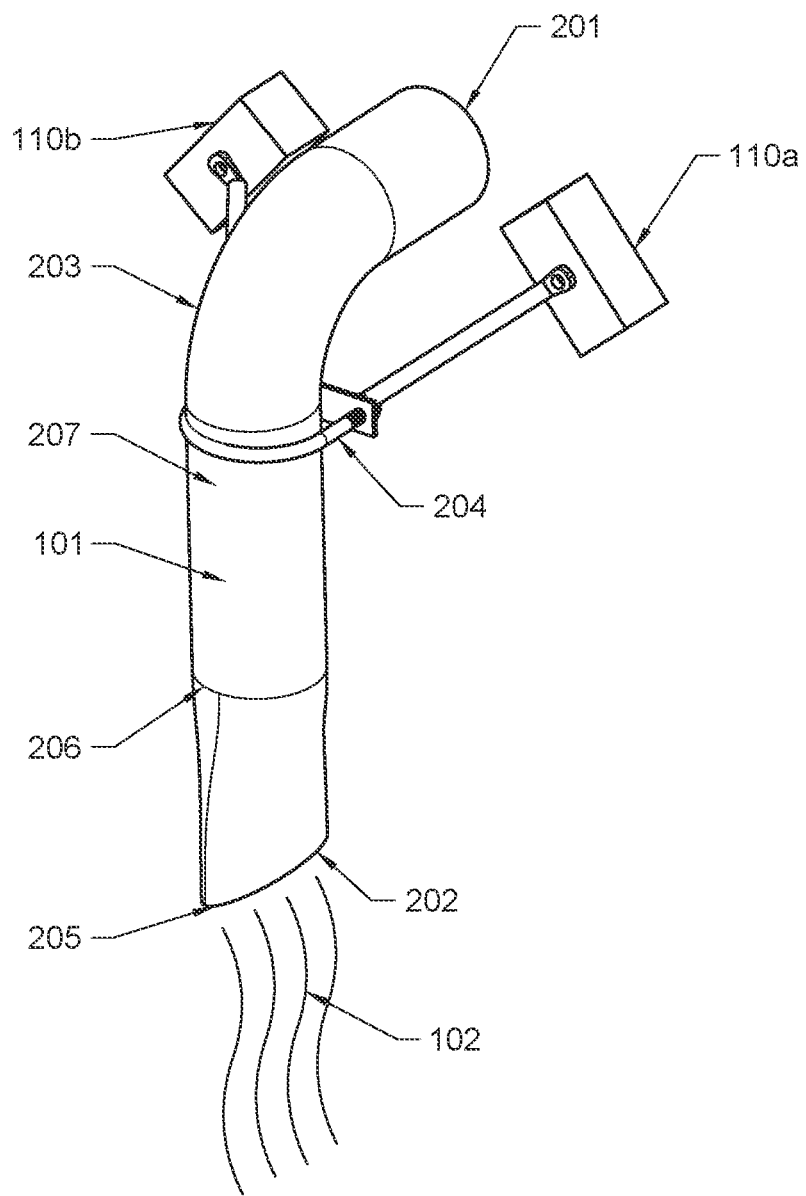
FIG. 2 is a 3D perspective of a profiling mount device without a dielectric profiling system sensor attached.

FIG. 2 is a 3D perspective of a profiling mount device 101 without a dielectric sensor 111 attached. The profiling mount device 101 is comprised of a tip 202, at least one angled pipe 203, and a connection point 201. Optionally, mounting brackets 110 and a mounting clamp 204 may further comprise the profiling mount device 101. The manner in which the profiling mount device 101 is mounted or attached to a compactor 103 can use any manner appreciated by a person with ordinary skill in the art. The only attachment requirements are that the connection point 201 must be secured to the exhaust port 107 such that it remains secured while the compactor 103 is in normal operations and maintains a seal between the connection point 201 and the exhaust port 107. The connection point 201 can be attached to the exhaust port 107 using welding methods, clamps, or other appreciated methods. A clamp may be an exhaust pipe clamp commonly understood by a person of ordinary skill in the art. Such exhaust pipe clamp is traditionally used to secure exhaust pipes together. Alternatively, a clamp may be of any shape that matches the exhaust port 107 and the connection point 201. A welding method is any method which fuses two materials together such to create a weld connection.

The angled pipe 203 is attached to the connection point 201 on the end opposite as to where the connection point 201 is secured to the exhaust port 107. A drop pipe 207 may optionally be attached between the angled pipe 203 and the tip 202. The angled pipe 203 is attached to the drop pipe 207, and the drop pipe 207 on the other end is attached to the tip 202. The drop pipe 207, when used in an embodiment, allows for the tip 202 to be positioned at a desired location relative to the asphalt surface 108. As an alternative embodiment, the angled pipe 203 may be attached to the tip 202. The angled pipe 203 redirects exhaust 102 to the tip 202 and the tip 202 directs the exhaust 102 onto the asphalt surface 108.

The connection point 201, the angled pipe 203, the tip 202, and the optional drop pipe 207 are configured such that they have an inner surface and an outer surface. The inner surface is in effect the inner surface of a pipe. The connection point 201, the angled pipe 203, the tip 202, and the optional drop pipe 207 need not be in the round shape of a traditional pipe and may comprise any shape that allows the exhaust to pass through. The exhaust passes through the connection point 201, the angled pipe 203, the tip 202, and the optional drop pipe 207 such that the exhaust 102 emitted from the exhaust port 107 is emitted out the tip 202 upon the asphalt surface 108 at a desired location. The connection point 201, the angled pipe 203, the tip 202, and the optional drop pipe 207 are considered the flow channel.

The tip 202 is located at the location on the profiling mount device 101 where exhaust 102 is emitted from the profiling mount device 101. The tip 202 is comprised of a tip opening 205 and a tip connection 206. The tip 202 may be in any shape that allows for exhaust 102 to flow through and be directed upon the desired location on the asphalt surface 108. In FIG. 2 the tip opening 205 is shown as narrowed straight opening.

Figure 3:
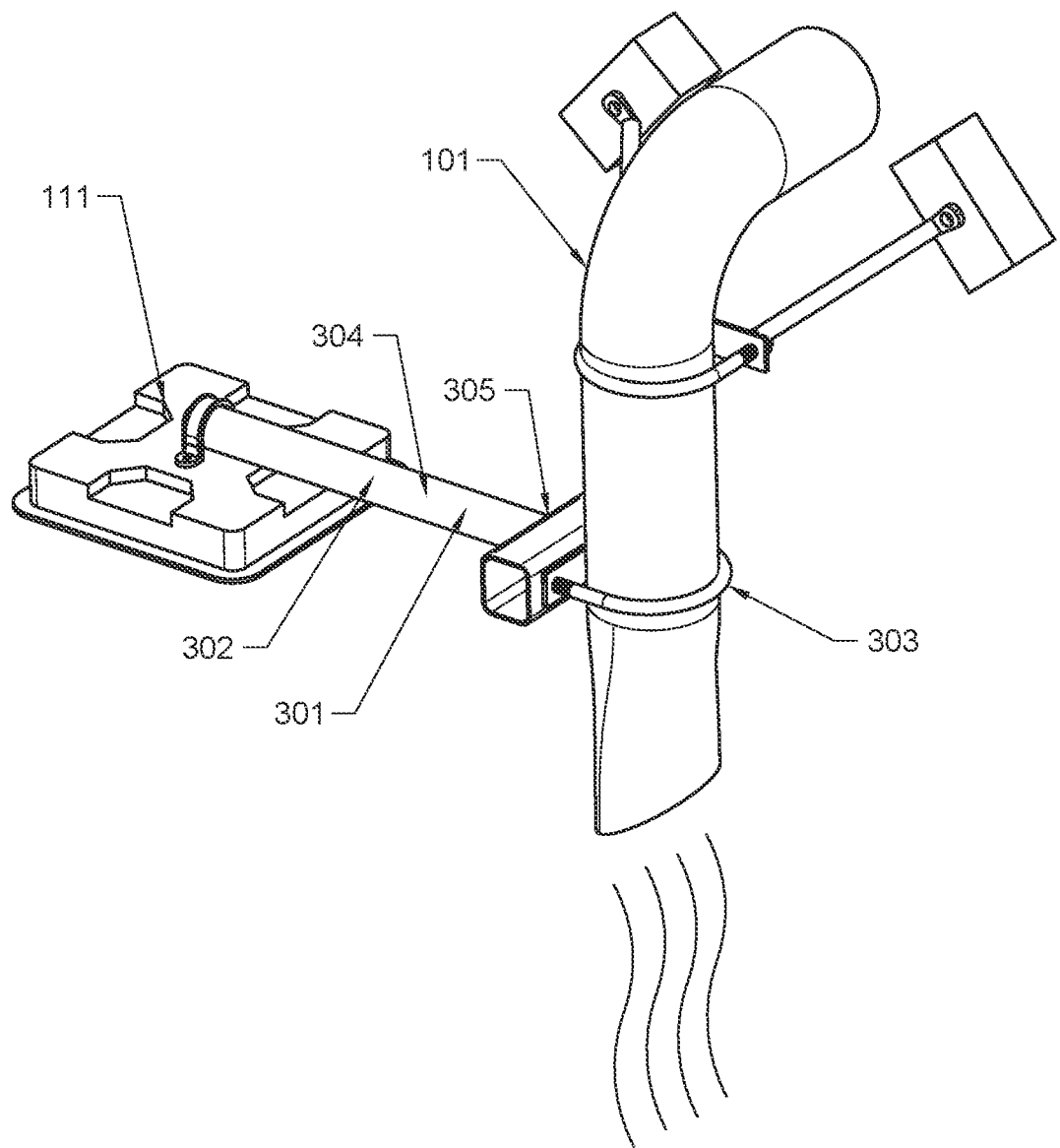
FIG. 3 is a 3D perspective of a profiling mount device with a dielectric profiling system sensor attached.

FIG. 3 is a 3D perspective of a profiling mount device 101 with a dielectric profiling system sensor attached. The dielectric profiling system sensor is a dielectric sensor 111. In the exemplary embodiment shown in FIG. 3 the profiling mount device 101 is shown as the same embodiment as shown in FIG. 2 but also shows a dielectric sensor 111 attached. The dielectric sensor 111 is attached using a dielectric mount 301. The exemplary dielectric mount 301 comprises an arm 302 and an arm bracket 303. The dielectric mount 301 may be attached anywhere upon the flow channel.

The arm bracket 303 is attached to profiling mount device 101. In the shown embodiment, a u-bolt type piece of hardware is used as the arm bracket 303. The u-bolt type arm bracket 303 is secured to the arm 302. Alternatively, the arm bracket 303 may be a manner of welding which attaches the arm 302 to the profiling mount device 101. The arm bracket 303 may also be configured as other hardware which can interface with the arm 302 and the profiling mount device 101.

In the shown embodiment, the arm 302 comprises a beam 304 and an optional tee head 305. The arm 302 may be configured in any way that connects the arm bracket 303 and the beam 304. The optional tee head 305 is used in the shown embodiment as a location on the arm where the shown u-bolt type arm bracket 303 is attached.

The beam 304 on the arm 302 is attached to the dielectric sensor 111 in such a way that allows for the dielectric sensor 111 to be positioned in a location that allows for the dielectric sensor 111 to take readings at a desired location on the asphalt surface 108. The manner in which the beam 304 is attached to the dielectric sensor 111 must be such that the dielectric sensor 111 does not move relative to the compactor 103, upon which the profiling mount device 101 is attached, when the compactor 103 is in normal operation.

Figure 4:
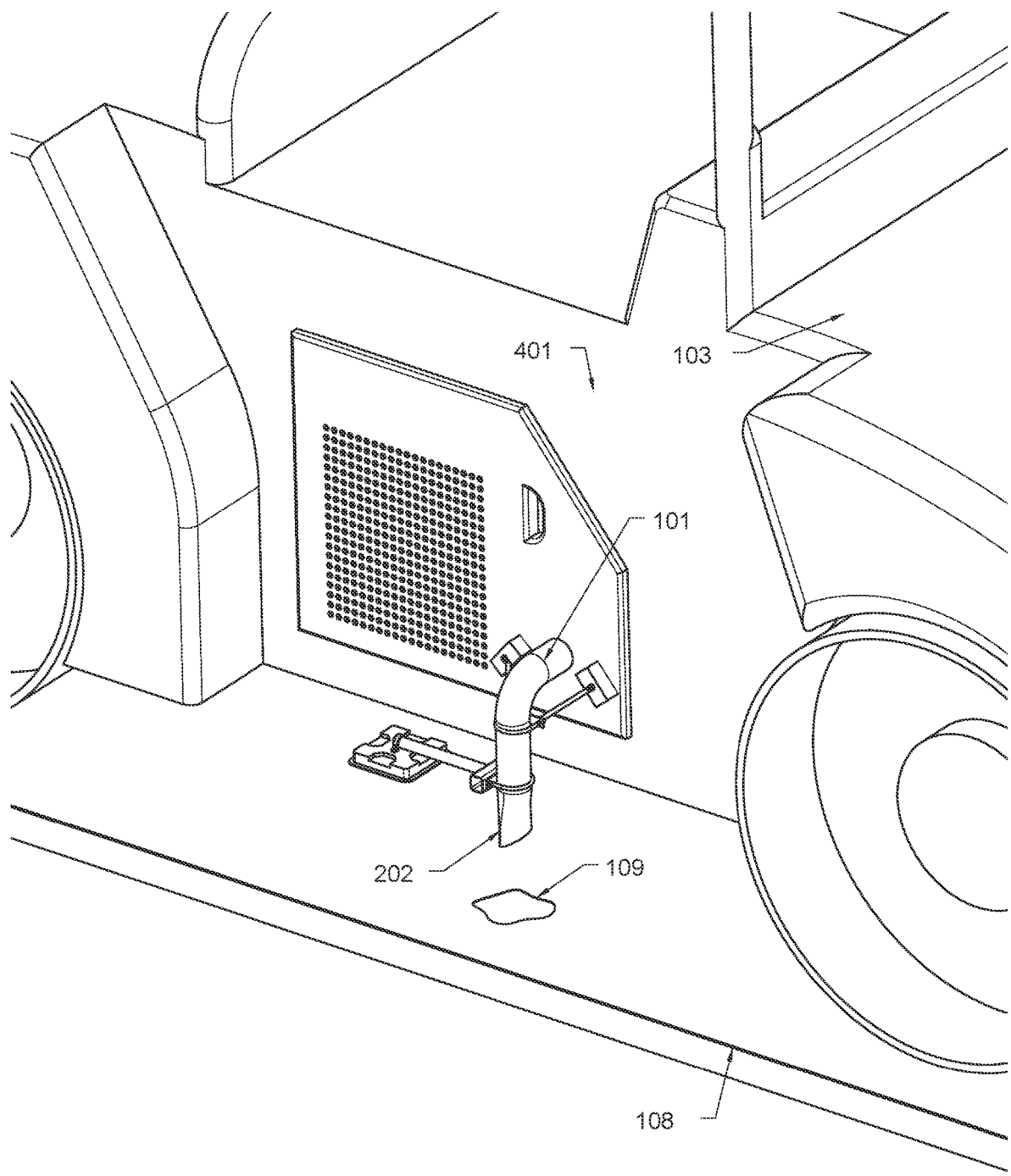
FIG. 4 is a 3D perspective of a compactor from an upper perspective with a profiling mount device attached which is positioned such to direct exhaust on surface moisture located on an asphalt surface.

FIG. 4 is a 3D perspective of a compactor 103 from an upper perspective with a profiling mount device 101 attached, which is positioned such to direct exhaust 102 on surface moisture 109 located on an asphalt surface 108. As shown in the exemplary embodiment, the profiling mount device 101 is positioned such to cause the tip 202 to direct exhaust 102 on an asphalt surface 108 which is within the surface area which the front roller 104 or rear roller 105 has or will respectively roll over. The compactor 103 has a vertical centerline plane 401. The vertical centerline plane 401 is the center of the compactor 103 along the direction of travel. The vertical centerline plane 401 is parallel to the compactor's direction of travel. The vertical centerline plane 401 is perpendicular to the asphalt surface 108.

In the exemplary embodiment, the front roller 104 and rear roller 105 extend further from the vertical centerline plane 401 of the compactor 103 than the tip 202. In other embodiments, the tip 202 may extend further from the vertical centerline plane 401 than the front roller 104 and rear roller 105. When the tip 202 is positioned further from the vertical centerline plane 401, the profiling mount device 101 is directing exhaust 102 on a location on the asphalt surface 108, which is not in the path which the front roller 104 or rear roller 105 has or will respectively roll over within the current line of travel. The angled pipe 203 and the drop pipe 207 may be configured to direct exhaust 102 on any location relative to the compactor 103, which is desired to be dried for the purpose of using the dielectric sensor 111 to take a sensor reading.

Figure 5:
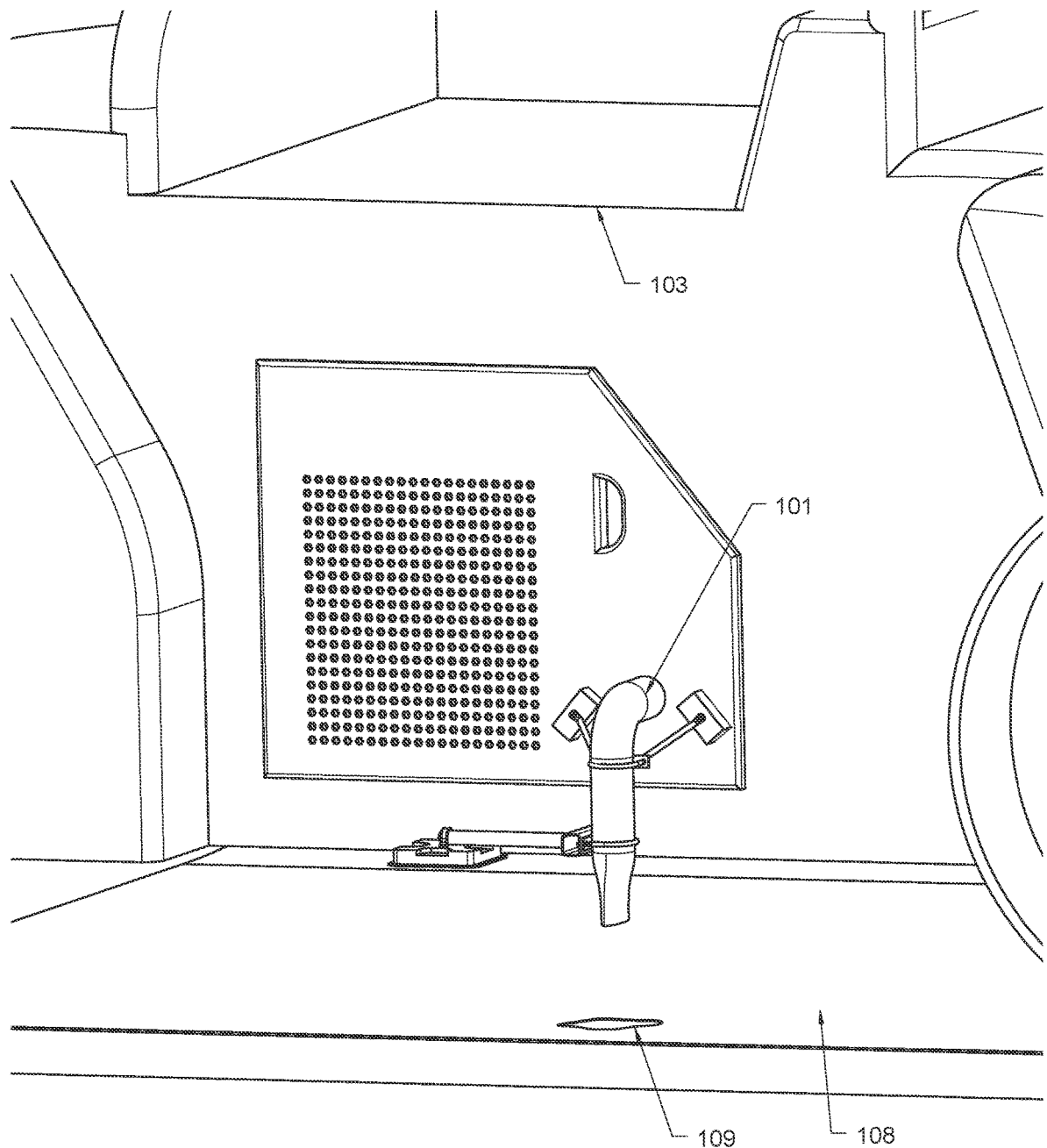
FIG. 5 is a 3D perspective of a compactor from a side profile with a profiling mount device attached which is positioned such to direct exhaust on surface moisture located on an asphalt surface.

FIG. 5 is a 3D perspective of a compactor 103 from a side profile with a profiling mount device 101 attached, which is positioned such to direct exhaust 102 on surface moisture 109 located on the asphalt surface 108. The profiling mount device 101 in the exemplary perspective is positioned relative to the asphalt surface 108 in a vertical position. In other terms, the profiling mount device 101 in the exemplary view is at a 90 degree angle relative to the asphalt surface 108. The exhaust port 107 has an opening through which exhaust 102 is emitted. An axis parallel to the flow of the exhaust at the center of the exhaust port 107 may be considered the axis of the exhaust port. The profiling mount device 101 may be rotated on the axis of the exhaust port. When rotating the profiling mount device 101 on the axis of the exhaust port, the profiling mount device 101 may be positioned at an acute or obtuse angle in relation to the asphalt surface 108. Positioning the profiling mount device 101 at different angles in relation to the asphalt surface 108 allows for surface moisture 109 to be dried in different manners and at different rates.

The material used to construct the profiling mount device 101 may be of any material which is capable of withstanding the pressure and temperature of the exhaust 102, which is produced by the power unit 106. In an embodiment wherein the power unit 106 is a diesel engine, the material used as an example may be steel, steel alloys, aluminum, cast iron, or ceramic. As shown in the figures, the flow channel is of a steel material.

In a roadway application, asphalt is commonly laid by a paver after which one or more compactors perform compaction. Three separate types of compactors often perform compaction. Each of these are a different type of compactor 103. The first stage is the knockdown roller, the second is the intermediate roller, and the third is a final roller. The final roller is sometimes referred to as the correction roller. The dielectric constant is generally measured after the final roller. Before taking a dielectric constant reading, the asphalt surface 108 must be dried of surface moisture 109. Traditionally, the asphalt section 112 is let to cool to a temperature of about 48.8 degrees Celsius (120 degrees Fahrenheit) prior to taking a dielectric constant reading. By allowing the asphalt section 112 to cool, the asphalt section 112 is given time to dry. Asphalt cures at a temperature of 60 degrees Celsius (140 degrees Fahrenheit) to 65.5 degrees Celsius (150 degrees Fahrenheit). By allowing the asphalt section 112 to cool to 48.8 degrees Celsius, the asphalt is cured and cannot be further compressed. Further, delaying the dielectric constant reading until the asphalt is cooled, results in the paver laying asphalt at a significant distance ahead of where the desired location where the dielectric constant reading is being taken. This means that any adjustment to be made with the asphalt installation process is not applied to the asphalt section 112 installed between the desired location where the dielectric constant reading is taken and where the paver is located.

The paver is part of a paving train when asphalt is being installed for a highway application. A paving train often comprises of a paver and one or more compactors. The paver receives asphalt from a hot plant which is delivered on trucks. The paver then lays the asphalt at the location where the roadway is desired. Behind the paver, one or more compactors compress the asphalt which was laid by the paver. Generally, the last compactor 103 to compress the asphalt is the final roller. For roadway applications, the compactor 103 on which the profiling mount device 101 is attached is generally the finish roller.

The profiling mount device 101 allows for a dielectric constant to be measured contemporaneously with a compactor 103 traveling over an asphalt surface 108. This allows for dielectric sensor readings to be taken much sooner after the asphalt section 112 is laid by a paver than traditional dielectric constant reading methods. Traditionally, dielectric constant reading methods which wait for the asphalt to cool to a temperature of about 48.8 degrees Celsius (120 degrees Fahrenheit) often cause the dielectric constant readings to be taken at a longer distance of over 1,000 meters (3,280 feet) from the paving train. The profiling mount device 101 allows for dielectric readings to be taken at a smaller distance from the paving train. Typically, the profiling mount device 101 can result in a dielectric constant reading being taken at a distance of less than 1,000 meters (3,280 feet) from the paving train. For example, a dielectric constant reading might be taken 152 meters (500 feet) from the paving train.

In an embodiment wherein the power unit 106 is a diesel engine, the exhaust 102 is expressed from the diesel engine at an increased pressure and an increased temperature. The pressure is increased relative to the air pressure outside of the profiling mount device 101. A diesel engine is an internal combustion engine that burns diesel fuel which results in diesel exhaust. Given the movement of the engine's internal components and expansion within the combustion chamber, the exhaust is expressed at an increased pressure. This increased pressure causes the exhaust to flow out of the exhaust port 107, through the profiling mount device 101, and onto the asphalt surface 108 at a desired location. The flow of the exhaust assists in blowing surface moisture 109 off of the asphalt surface 108. The increased temperature of the diesel exhaust further has a drying effect on the surface moisture 109. It is common for diesel exhaust to range in temperature from 540 degrees Celsius to 650 degrees Celsius (1,000 degrees Fahrenheit to 1,200 degrees Fahrenheit). Surface moisture 109 generally comprises primarily of water molecules with an evaporation temperature of less than the temperature of diesel exhaust.

Compaction equipment is used to compress new asphalt, which is laid on a roadway. An asphalt section 112 is compacted to certain specifications based on engineering and design requirements. Engineering and design requirements include the steps of establishing a mix design, testing the mix for optimal compaction, and establishing the dielectric constant required to achieve the optimal compaction. Specifications often call for compaction such that a specified density is achieved. Density is a measurement taken to derive the percentage air voids in an asphalt section.

A commonly desired density range is between 91-96%. In the event the density constant is too low, the asphalt may need to be removed and replaced. Removal and replacement is costly for the contractor or owner of the project. Alternatively, if the density is too high, the contractor installing the asphalt may be penalized. Structurally, it is thought that the asphalt is weakened from seasonal freeze-thaw cycles when the density is too high. Additionally, it is common that if the contractor is able to achieve a density within a narrow constraint, the contractor is paid bonuses. An exemplary narrow constraint is a density of 93-95%. Traditional density methods which cause readings to be taken at a longer distance relative to the paving train, allow for less fine tuning and therefore less ability to cause the density to fall within a narrow constraint.

Explanation of Exemplary Language

While various inventive aspects, concepts and features of the general inventive concepts are described and illustrated herein in the context of various exemplary embodiments, these various aspects, concepts and features may be used in many alternative embodiments, either individually or in various combinations and sub-combinations thereof.

Unless expressly excluded herein all such combinations and sub-combinations are intended to be within the scope of the general inventive concepts. Still further, while various alternative embodiments as to the various aspects, concepts and features of the inventions (such as alternative materials, structures, configurations, methods, devices and components, alternatives as to form, fit and function, and so on) may be described herein, such descriptions are not intended to be a complete or exhaustive list of available alternative embodiments, whether presently known or later developed. Those skilled in the art may readily adopt one or more of the inventive aspects, concepts or features into additional embodiments and uses within the scope of the general inventive concepts even if such embodiments are not expressly disclosed herein. Additionally, even though some features, concepts or aspects of the inventions may be described herein as being a preferred arrangement or method, such description is not intended to suggest that such feature is required or necessary unless expressly so stated. Still further, exemplary or representative values and ranges may be included to assist in understanding the present disclosure; however, such values and ranges are not to be construed in a limiting sense and are intended to be critical values or ranges only if so expressly stated. Moreover, while various aspects, features and concepts may be expressly identified herein as being inventive or forming part of an invention, such identification is not intended to be exclusive, but rather there may be inventive aspects, concepts and features that are fully described herein without being expressly identified as such or as part of a specific invention. Descriptions of exemplary methods or processes are not limited to inclusion of all steps as being required in all cases, nor is the order that the steps are presented to be construed as required or necessary unless expressly so stated.

What is claimed is:

1. A profiling mount device comprising:
    a connection point attached to an exhaust port on a compactor wherein a power unit is attached to the compactor, wherein the power unit emits an exhaust energy as an exhaust, wherein the exhaust is emitted through the exhaust port, wherein the exhaust passes through the connection point;
    an angled pipe attached to the connection point wherein the angled pipe redirects the exhaust;
    a tip attached to the angled pipe, wherein the exhaust is emitted through a tip opening upon a desired location on an asphalt surface, wherein the connection point, the angled pipe, and the tip comprise a flow channel; and
    a dielectric mount attached to the flow channel, wherein the dielectric mount comprises an arm, wherein a dielectric sensor may be attached to the arm, wherein the dielectric sensor may be positioned to take sensor readings at the desired location upon the asphalt surface.

2. The profiling mount device of claim 1, wherein the flow channel is of a steel material.

3. The profiling mount device of claim 1, wherein the connection point is attached to the exhaust port using a weld.

4. The profiling mount device of claim 1, wherein the connection point is attached to the exhaust port using a clamp.

5. The profiling mount device of claim 1, wherein a surface moisture is located at the desired location.

6. The profiling mount device of claim 1, wherein the compactor is a final roller.

7. The profiling mount device of claim 1, wherein the power unit is a diesel engine.

8. The profiling mount device of claim 1, wherein the dielectric sensor takes a dielectric constant reading.

9. The profiling mount device of claim 8, wherein the dielectric constant reading is used to determine density of an asphalt section.

10. A profiling mount device comprising:
    a connection point attached to an exhaust port on a compactor wherein a power unit is attached to the compactor, wherein the power unit emits an exhaust energy as an exhaust, wherein the exhaust is emitted through the exhaust port, wherein the exhaust passes through the connection point, wherein the compactor is a final roller, wherein the power unit is a diesel engine;
    an angled pipe attached to the connection point wherein the angled pipe redirects the exhaust;
    a tip attached to the angled pipe, wherein the exhaust is emitted through a tip opening upon a desired location on an asphalt surface, wherein the connection point, the angled pipe, and the tip comprise a flow channel, wherein the flow channel is of a steel material, wherein a surface moisture is located at the desired location; and
    a dielectric mount attached to the flow channel, wherein the dielectric mount comprises an arm, wherein a dielectric sensor may be attached to the arm, wherein the dielectric sensor may be positioned to take sensor readings at the desired location upon the asphalt surface.

11. A method of drying surface moisture on an asphalt surface comprising:
    expressing an exhaust from a power unit out of an exhaust port through a flow channel, wherein the power unit is attached to a compactor;
    emitting the exhaust through an angled pipe and through a tip onto a desired location on an asphalt surface;
    drying a surface moisture at the desired location on the asphalt surface with the exhaust; and
    reading a dielectric constant at the desired location on the asphalt surface with a dielectric sensor.

* * * * *